United States Patent [19]

Lindemans

[11] 4,402,330
[45] Sep. 6, 1983

[54] BODY IMPLANTABLE LEAD

[75] Inventor: Fredric W. Lindemans, Minneapolis, Minn.

[73] Assignee: Medtronic, Inc., Minneapolis, Minn.

[21] Appl. No.: 261,718

[22] Filed: May 8, 1981

Related U.S. Application Data

[63] Continuation of Ser. No. 78,090, Sep. 24, 1979, abandoned.

[51] Int. Cl.³ .............................................. A61N 1/04
[52] U.S. Cl. .................................. 128/786; 128/419 P
[58] Field of Search .................... 128/419 P, 639, 772, 128/784–788

[56] References Cited

U.S. PATENT DOCUMENTS

| | | | |
|---|---|---|---|
| 3,087,486 | 4/1963 | Kirkpatrick | 128/419 P |
| 3,222,755 | 12/1965 | Grass | 128/639 |
| 3,516,412 | 6/1970 | Ackerman | 128/786 |
| 3,890,977 | 6/1975 | Wilson | 128/785 |
| 4,020,829 | 5/1977 | Wilson et al. | 128/772 |

*Primary Examiner*—William E. Kamm
*Attorney, Agent, or Firm*—Everett J. Schroeder; Kenneth D. Siegfried; Robert O. Vidas

[57] ABSTRACT

A lead for a body implantable electrical stimulation system including at least one electrical conductor and electrical insulation which together define a flexible lead body. A stiffening system, in the form of a member coiled about a portion of the lead body, is provided to enhance the ability of that lead body portion to maintain its orientation in the presence of external forces, including forces imparted to the lead by movement of the body as well as gravity. Preferably, the coiled member is a multifilar member and, in a preferred embodiment, is a close wound trifilar member. The desired lead body orientation may be a straight or curved configuration and, in the latter instance, the lead body may be provided with a lumen such that the curve is extended or straightened on insertion of a stylet of sufficient stiffness. A body compatible material may overlie the coiled member to provide a smooth exterior surface at the stiffened lead body portion and, in a preferred embodiment, extends beyond the lead body portion to provide a stiffness transition region adjacent the coiled member.

7 Claims, 3 Drawing Figures

BODY IMPLANTABLE LEAD

This is a continuation of application Ser. No. 6/078,090, filed Sept. 24, 1979, now abandoned.

BACKGROUND OF PRIOR ART

Electrode positioning and position maintenance is a problem in many body stimulation contexts. Electrode position has been maintained through the use of sutures and electrode configurations which penetrate the body tissue itself. In addition, projections or tines have been employed to engage the body tissue to maintain the electrode in position. However, in some stimulation contexts, including temporary stimulation, such mechanical position maintenance devices are undesirable. For example, in the temporary stimulation context, such devices hinder the removal of the stimulation delivering lead. Electrode positioning, and electrode position maintenance, have also been accomplished by forming the lead body in various configurations.

One system by which a particular configuration may be established in a body stimulation lead is disclosed in U.S. Pat. No. 3,890,977, issued June 24, 1975 to Bruce C. Wilson for Kinetic Memory Electrodes, Catheters and Cannulae. In accordance with the Wilson disclosure, a lead may incorporate a material having a heat-activated mechanical memory. The desired configuration is established and the material annealed at high temperature. As the material cools to a temperature below its transitional temperature, it is reformed into a shape selected for ease of insertion. With the lead located at the desired position, the material having a mechanical memory is heated above its transitional temperature thereby returning it to its annealed shape. In this manner, a lead in accordance with the Wilson teaching can be configured for ease of insertion and reconfigured for anchoring or proper positioning of the lead electrode. However, at least at temperatures below the transitional temperature, the Wilson structure is not resilient as evidenced by its ability to be reformed for ease of insertion.

Another system whereby a desired configuration may be established in a body stimulation lead is disclosed in U.S. Pat. No. 3,729,008, issued Apr. 24, 1973 to Barough V. Berkovits for ELECTRODE FOR ATRIAL PACING WITH CURVED END FOR ATRIAL WALL ENGAGEMENT. In accordance with the Berkovits teaching, a portion of the lead body is provided with a curved configuration and additional insulation is applied at the area of curvature to cause the lead to assume the desired shape. While this approach may be initially effective, most known materials which are suitable for insulation of a body implantable lead also have a tendency to creep which, in time, causes the lead to depart from the desired configuration thus affecting the ability of the lead to retain the electrode in the desired position. The additional insulation also increases the bulk of the lead.

An additional system which facilitates the positioning of an electrode is disclosed in U.S. Pat. No. 3,516,412, issued June 23, 1970 to B. Ackerman for Bipolar Electrode Having Irregularity at Inserting End Thereof and Method of Insertion. The Ackerman system employs a lead having an electrode at its distal end with a second electrode being coiled around the lead through the entirety of its length. The coiled electrode provides a "linear irregularity" close to the distal electrode which irregularity provides an indication that the lead has been inserted a sufficient distance through a needle. The "linear irregularity" also assists in positioning the electrode. However, so as to maintain a flexibility throughout the lead, the material forming the coiled second electrode is extremely flexible which limits the force which may be applied by the irregularity to maintain the electrode in position.

BRIEF SUMMARY OF THE INVENTION

The present invention provides a lead for electrical body stimulation wherein a portion of the lead body, formed of a conductor and its insulation, has imparted thereto a resilient orientation maintaining stiffness which assists in the positioning of an electrode and the maintenance of that electrode position, resiliently and without creep. A member is coiled about the lead body portion and formed in the desired configuration to maintain that lead body portion in said configuration. Preferably, the coiled member is a multifilar member and, in a preferred embodiment, is a close wound trifilar member. The desired configuration may be a curve with the lead body being provided with a lumen such that the curve is extendable on insertion of a stylet of sufficient stiffness in the lumen. Material may be applied over the coiled member to provide a smooth exterior throughout the lead length and the material may extend beyond the coiled member to provide a stiffness transition region adjacent the coiled member.

DETAILED DESCRIPTION OF INVENTION

Figure 1:
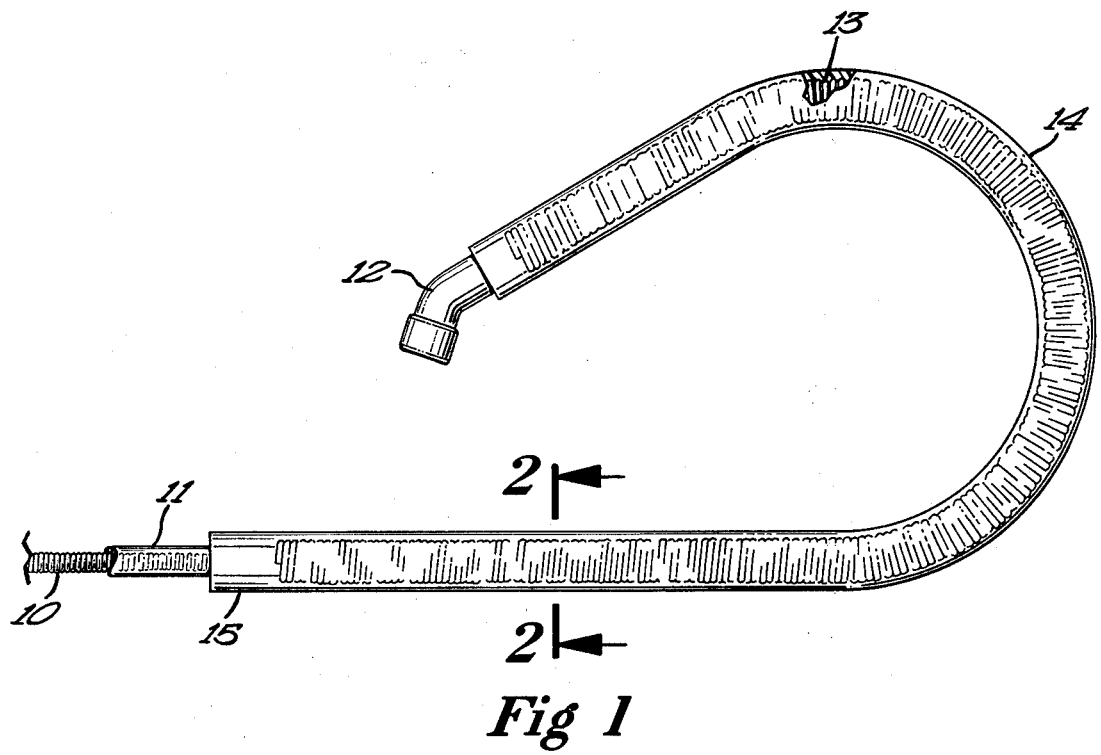
FIG. 1 illustrates a portion of a lead constructed in accordance with the principles of the present invention.

Referring now to FIG. 1, there is illustrated a preferred embodiment of a lead constructed in accordance with the present invention including a lead body formed of a conductor 10 and its insulation 11. The conductor 10 extends between an electrode 12 and a suitable connector assembly (not shown) for interconnection with a source of stimulation energy or, directly to the source of stimulation energy itself (not shown), all in known manner.

A flexible member 13 is coiled around a portion of the lead body formed of the conductor 10 and insulation 11, coiled member 13 being a resilient member of sufficient stiffness to impart and maintain a desired orientation to that lead body portion which coiled member 13 overlies. In FIG. 1, the orientation is a J-configuration similar to that illustrated in U.S. Pat. No. 3,729,008, which configuration is particularly suitable for atrial cardiac pacing. However, the coiled member 13 is capable of resiliently maintaining this configuration without the tendency to creep as found in the referenced patent. Thus, a resilient orientation maintaining stiffness is imparted to a portion of the lead body by the present invention of a type which is not present in the prior art. Indeed, the orientation maintained by coiled member 13 need not be the J-configuration illustrated in FIG. 1. In some contexts, it may be desirable that a portion of the lead body be maintained in some other configuration, including a straight configuration. Coiled member 13 is capable of imparting a stiffness to any desired lead body portion for maintaining any desired configuration. Coiled member 13 is "nonconducting" in the sense that it is not connected to conduct electricity, although it may be of a material which is electrically conductive.

An insulating material 14 may be applied over the coiled member 13 to provide a smooth exterior surface which will reduce the tendency for thrombus growth on the otherwise relatively rough exterior surface of the coiled member 13. Member 14 may extend beyond the lead body portion over which the member 13 is coiled, as at 15, to provide a stiffness transition region adjacent the member 13.

Figure 2:
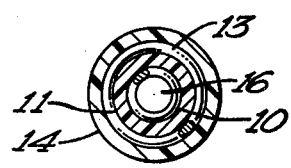
FIG. 2 is a cross-section taken along the line 2—2 in FIG. 1.

A preferred construction of a lead in accordance with the present invention is illustrated in FIG. 2 which is a cross-section taken along the line 2—2 in FIG. 1. In FIG. 2, the conductor 10 is shown as a coil having a central lumen 16. Insulation 11 surrounds the coil 10 and may be a preformed tubular member as will be described more fully below. The coiled member 13 overlies the insulation 11 while the insulation 14 surrounds the coiled member 13. Member 14 may be a preformed tubular member similar to member 11.

It is known that polyurethane will expand on immersion in acetone. Thus, the conductor 10 may be formed with electrode 12 in position. A tubular member 11, formed of polyurethane, may then be expanded in acetone such that the conductor 10 can be easily threaded therethrough. After the tubular member 11 has returned to its original size, the lead body formed of the conductor 10 and insulation 11 may be threaded through the coiled member 13 which is preferably preformed in the desired configuration. Threading is continued until coiled member 13 overlies the lead body portion where the resilient orientation maintaining stiffness is desired. Member 14 may then be expanded in acetone and the assembly then threaded therethrough such that the member 14 overlies the coiled member 13. Alternatively, the lead of the present invention may be constructed by a molding process with the insulation members 11 and 14 being molded in place, in known manner. However, polyurethane is a tougher material than most material used in molded lead assemblies. Thus, a lead constructed with preformed polyurethane tubular members, as described above, can have a smaller diameter than such molded constructions. This is particularly true relative to U.S. Pat. No. 3,729,008, discussed above, which provides additional insulation for configuration establishment and maintenance.

Figure 3:
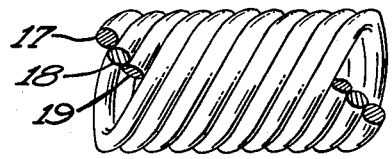
FIG. 3 illustrates a preferred configuration of a portion of the embodiment illustrated in FIG. 1.

The lumen 16 formed within conductor 10 will accept a stylet and, if the stylet is of sufficient stiffness, its insertion will extend or straighten a curve in the lead body portion established by the coiled member 13. Typically, the coiled member 13 will be formed of a material having a circular cross-section with many factors affecting its stiffness. For example, such factors as the characteristics of the material employed, the spacing between adjacent coils, the length of the lead body portion that it is desired to stiffen and the number of filars used to form the coiled member 13 will all affect the stiffness of that member. A multifilar member will allow a smaller diameter wire to be used while attaining the same stiffness. A close wound trifilar coil member has provided satisfactory results relative to the stiffness attained. Such a trifilar close would coil is illustrated in FIG. 3 with the three filars being designated as 17, 18 and 19.

Obviously, many modifications and variations of the present invention are possible in light of the above teachings. For example, more than one conductor can be contained within insulation 11 with the lead being provided with additional electrodes, in known manner. It is therefore to be understood that, within the scope of the appended claims, the invention may be practiced otherwise than as specifically described.

I claim:

1. In a lead for a body implantable electrical stimulation system of the type having electrical conducting means and means electrically insulating said conducting means, said conducting and insulating means defining a flexible lead body, the improvement which comprises non-conducting, multifilar means coiled about a portion of said lead body for imparting a resilient orientation maintaining stiffness to said lead body portion and means overlying said coiled means to provide a smooth exterior surface at said lead body portion, said overlying means comprising means extending beyond said lead body portion and coiled means for providing a stiffness transition region adjacent said lead body portion.

2. The lead of claim 1 wherein said coiled means comprises close wound trifilar means.

3. The lead of claim 1 wherein said coiled means comprises means formed in a desired configuration to maintain said lead body portion in said configuration.

4. The lead of claim 1 wherein said desired configuration is an extendable curve, said lead body being provided with a stylet lumen and said curve being extendable on insertion of a stylet in said lumen.

5. The lead of claim 4 wherein said coiled means comprises close wound trifilar means.

6. The lead of claim 1 wherein said insulating means comprises molded means, said molded means establishing said curve at said lead body portion.

7. The lead of claim 1 wherein said insulating means comprises preformed tubular means.

* * * * *

UNITED STATES PATENT AND TRADEMARK OFFICE
CERTIFICATE OF CORRECTION

PATENT NO. : 4,402,330
DATED : September 6, 1983
INVENTOR(S) : Fredric W. Lindemans It is certified that error appears in the above-identified patent and that said Letters Patent are hereby corrected as shown below:

Column 2, line 27, the word "surface" should be inserted before the word "throughout".

Signed and Sealed this

Eighth Day of November 1983

[SEAL]

Attest:

GERALD J. MOSSINGHOFF

Attesting Officer   Commissioner of Patents and Trademarks